(12) United States Patent
Wu et al.

(10) Patent No.: US 6,355,851 B1
(45) Date of Patent: Mar. 12, 2002

(54) CUMENE SYNTHESIS PROCESS USING PURIFIED BENZENE AND PROPYLENE FEEDSTOCK STREAMS

(75) Inventors: Albert H. Wu, Medford, NJ (US); James T. Wei, Glen Mills, PA (US)

(73) Assignee: Sunoco, Inc. (R&M), Philadelphia, PA (US)

(*) Notice: Subject to any disclaimer, the term of this patent is extended or adjusted under 35 U.S.C. 154(b) by 0 days.

(21) Appl. No.: 09/711,285

(22) Filed: Nov. 13, 2000

Related U.S. Application Data

(63) Continuation-in-part of application No. 09/359,556, filed on Jul. 22, 1999, now abandoned.

(51) Int. Cl.$^7$ .................................................. C07C 2/66
(52) U.S. Cl. ........................................ 585/448; 585/467
(58) Field of Search .................................. 585/448, 467

(56) References Cited

U.S. PATENT DOCUMENTS

| | | | | |
|---|---|---|---|---|
| 2,403,879 A | * | 7/1946 | Schulze et al. | 585/314 |
| 2,473,206 A | * | 6/1949 | Jones | 208/260 |
| 2,500,755 A | * | 3/1950 | Jones | 208/99 |
| 4,137,154 A | * | 1/1979 | Audeh | 208/254 R |
| 4,358,362 A | * | 11/1982 | Smith et al. | 208/91 |
| 4,992,606 A | * | 2/1991 | Kushnerick et al. | 585/467 |
| 5,077,445 A | * | 12/1991 | Le | 585/467 |
| 5,730,860 A | * | 3/1998 | Irvine | 208/213 |

FOREIGN PATENT DOCUMENTS

| WO | WO 99 07673 A | 2/1998 |
|---|---|---|

OTHER PUBLICATIONS

Synthetic zeolites and other microporous oxide molecular sieves, Sherman JD: *Proc. Natl. Acad. Sci. USA* Mar. 1999;vol. 96 (3471–3478).

Sulphonic acid cation–exchangers as catalysts in the refining of phenol and aromatic hydrocarbons, Zieborak, K and Ratajczak W: *Chemistry and Industry* Jul. 4, 1983; (516–518).

Petroleum Refining Processes, Section III: Chapter 2 pp. 1–64 Source: Internet.

\* cited by examiner

*Primary Examiner*—Thuan D. Dang
(74) *Attorney, Agent, or Firm*—Robert A. Koons, Jr.; Matthew P. McWilliams; Pepper Hamilton LLP

(57) ABSTRACT

A zeolite-catalyzed cumene synthesis process in which benzene and propylene feedstocks are pre-treated to remove catalyst poisons. The benzene feedstock is pre-treated under pressure by contact with a "hot" clay bed at a temperature of about 200 to 500° C., followed by distillation of the benzene feedstock to separate the benzene from the higher molecular weight materials formed from olefinic poisons during the hot clay treatment. The benzene feed is also subjected to a "cold" clay treatment wherein the benzene distillate is contacted with an ambient-temperature clay. The propylene feedstock is pre-treated by contact with an alumina to remove trace sodium compounds and moisture, a molecular sieve to remove moisture, and two modified aluminas to remove catalyst poisons. The pre-treated propylene and benzene feedstocks are then reacted in the presence of a zeolite catalyst to form cumene without causing rapid degradation of the catalyst's activity.

4 Claims, 1 Drawing Sheet

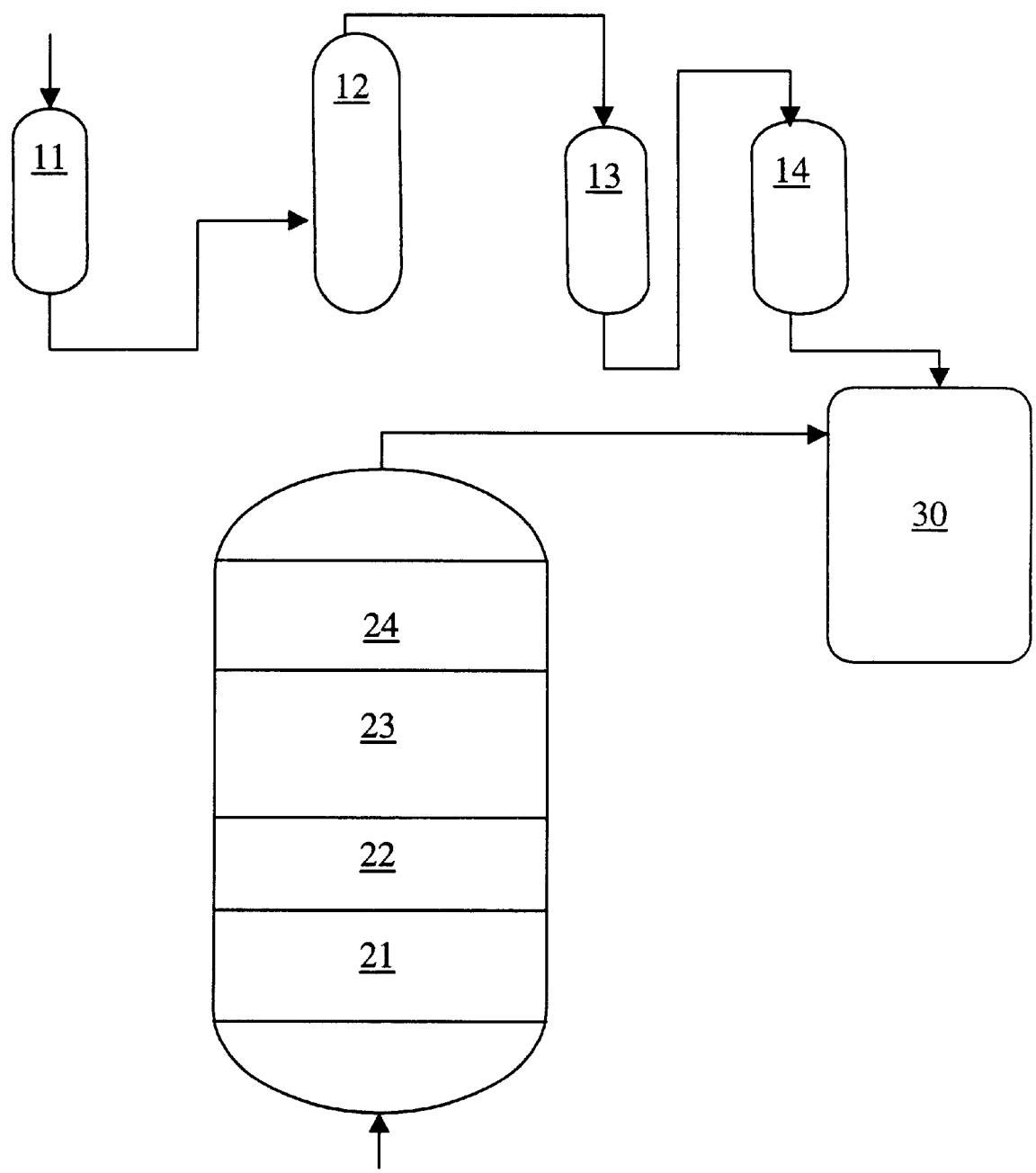
Figure

CUMENE SYNTHESIS PROCESS USING PURIFIED BENZENE AND PROPYLENE FEEDSTOCK STREAMS

This is a continuation-in-part of application Ser. No. 09/359,556 filed on Jul. 22, 1999 now abandoned.

FIELD OF THE INVENTION

The invention relates to a process for synthesizing cumene, and more particularly to a zeolite-catalyzed process for synthesizing cumene involving pre-treating benzene and propylene feedstocks to remove catalyst poisons.

BACKGROUND OF THE INVENTION

Zeolite catalysts, particularly versions of the present generation of catalysts, are very effective for catalyzing industrial-scale cumene synthesis via benzene/propylene reactions. While their catalytic efficacy is impressive, most zeolites are highly susceptible to nitrogen-, sulfur- and oxygen-containing contaminants and olefinic contaminants. These contaminants, also referred to as "poisons," deactivate the catalyst by blinding (i.e., clogging) the zeolite's active sites. Since almost all untreated industrial grade benzene and propylenes contain enough poisons to rapidly and significantly degrade the catalytic activity of zeolite catalysts, an effective and low-cost method of stripping the catalyst poisons from the feedstocks would extend the life of the zeolite catalyst and improve the efficiency of zeolite-catalyzed cumene synthesis.

SUMMARY OF THE INVENTION

Briefly, the invention relates to a zeolite-catalyzed cumene synthesis process in which benzene and propylene feedstocks are pre-treated to remove catalyst poisons. The benzene feedstock is pre-treated by contact with a "hot" clay bed, the hot clay bed being at a temperature of about 200 to 500° F., preferably about 350 to 500° F. and more preferably 350 to 375° F., under a pressure sufficient to maintain a substantial portion of the feedstock in a liquid phase. The benzene feedstock is thereafter distilled to separate the benzene from the higher molecular weight materials formed from olefinic poisons during the hot clay treatment. The benzene distillate is also subjected to a "cold" clay treatment wherein the benzene distillate is contacted with an ambient-temperature clay to remove nitrogen-containing catalyst poisons.

The propylene feedstock is pre-treated by contact with an alumina to remove trace sodium compounds and moisture, a molecular sieve to remove moisture, and two modified aluminas to remove catalyst poisons. The pre-treated propylene and benzene feedstocks are then reacted in the presence of a zeolite catalyst to form cumene without causing rapid degradation of the catalyst's activity.

BRIEF DESCRIPTION OF THE DRAWING

The FIGURE is a schematic depiction of a cumene synthesis unit set up for a cumene synthesis process in accordance with the invention.

DETAILED DESCRIPTION OF THE INVENTION

The cumene synthesis method of the invention utilizes multi-step pre-treatments of benzene and propylene feedstocks. The pre-treatments together maximize catalyst activity and lifespan, thereby providing a highly-efficient cumene synthesis process.

Prior to pre-treatment, the benzene feedstock used in the present invention contains olefinic and/or nitrogen-containing catalyst poisons. To remove the olefinic contaminants, which generally have boiling points similar to benzene, the benzene feedstock is contacted with a "hot" clay, i.e., a clay at about 200–500° F., preferably about 350–500° F., and more preferably at a temperature of 350–375° F., at a pressure suitable for maintaining the benzene feedstock in liquid phase (for example, about 200 psig at a temperature of 350–375° F.). The clay or clays used in this hot pre-treatment are not particularly limited so long as they are capable of converting olefinic contaminants in the benzene feedstock to polymers, alkylaromatics or other hydrocarbons possessing higher boiling points than benzene so that they may be separated from the benzene feedstock by distillation. As examples, the clay may include bentonites, bauxites and/or mordenites. The clay may be acid-treated to increase active acid sites and surface area. The manner in which the hot clay and benzene feed are contacted is not particularly limited, so long as the conversion of olefinic contaminants as described above is enabled; those of ordinary skill in the art can control this contacting in accordance with the purity of the benzene feedstock and the sensitivity of the zeolite catalyst used in the cumene reaction to olefinic contaminants. Preferably, the clay is arranged in a clay bed for the benzene/clay contacting.

After the hot clay treatment, the benzene feedstock is distilled to separate the lower-boiling benzene from the higher-boiling converted olefinic contaminants. Any distillation means that is capable of separating the low boiling benzene from the higher boiling converted olefinic contaminants may be used, and the appropriate balance between distillation efficiency and throughput can be evaluated and controlled by those of ordinary skill in the art according to the contaminant content in the feedstock and the sensitivity of the zeolite catalyst to those contaminants.

Either before the hot clay treatment or, preferably, after the hot clay treatment and distillation, the benzene feedstock is subjected to a "cold" clay treatment wherein the feedstock is contacted with an ambient temperature clay capable of removing nitrogen-containing poisons from the feedstock. Any clay or combination of clays capable of adsorbing nitrogen-containing contaminants found in benzene feedstocks may be used, examples of which include bentonites, bauxites and/or mordenites. The manner in which the cold clay and benzene feedstock are contacted is not particularly limited, so long as the contacting is sufficient to remove at least a portion of the nitrogen-containing catalyst poisons present in the benzene feedstock. Preferably, the clay is arranged in a clay bed for the benzene/clay contacting, and more preferably the clay is arranged in a series of two or more beds.

The invention also involves pre-treating the propylene feedstock prior to the benzene/polypropylene reaction. In addition to propylene, the propylene feedstock may comprise propane, the quantity of propane being preferably about 25 wt %. The un-treated propylene feedstock contains nitrogen-, oxygen- and/or sulfur-containing catalyst poisons that are at least partially removed by the pre-treatment steps of the invention.

The propylene feedstock is first contacted with an alumina to remove trace sodium compounds and moisture. The removal of trace sodium compounds protects the downstream modified-alumina adsorbents and the zeolite catalyst which are both susceptible to damage from sodium compounds, while the removal of moisture preserves the adsorptivity of the downstream modified aluminas for nitrogen-, oxygen- and/or sulfur-containing poisons. Any form or forms of alumina capable of adsorbing sodium compounds and moisture may be used, a preferred example being ALCOA's F-200® alumina. The manner in which the alumina and propylene feedstock are contacted is not particularly limited, so long as the contacting is sufficient to remove at least a portion of the moisture and trace sodium compounds present. To enhance the efficiency of the sodium compound removal, the propylene feedstock may be water washed prior to the contacting.

After the alumina treatment, the propylene feed is contacted with a molecular sieve that removes additional moisture from the propylene feed. This step enhances the removal of nitrogen-, oxygen- and/or sulfur-containing poisons by modified aluminas in subsequent steps. Any molecular sieve capable of removing moisture may be used, a preferred example being Zeochem molecular sieve 3A Z3-04®, a product of United Catalyst, Inc. of Louisville, Ky. The manner in which the propylene feed and molecular sieve are contacted is not particularly limited, so long as the contacting is sufficient to remove at least a portion of the moisture present.

After the treatment with the molecular sieve, the propylene feed is contacted with a first modified alumina capable of adsorbing nitrogen-, oxygen- and sulfur-containing contaminants from the propylene feed. Any modified alumina capable of removing these poisons may be used, an example of which is sold under the trademark SELEXSORB-CDX by ALCOA. The manner in which the propylene feed and first modified alumina are contacted is not particularly limited, so long as the contacting is sufficient to remove at least a portion of the nitrogen-, oxygen- and sulfur-containing contaminants present. As suggested above, since the adsorption efficiency of these types of modified aluminas is typically diminished by water, the moisture removal provided by the alumina and molecular sieve treatments preceding the first modified alumina treatment protects the modified alumina used in this step.

Either before or after the first modified alumina treatment, but preferably after, the propylene feed is contacted with a second modified alumina capable of adsorbing hydrogen sulfide and carbonyl sulfide. Hydrogen sulfide and carbonyl sulfide are particularly harmful to the activity of zeolite catalysts, and they are likewise undesirable contaminants in the cumene end-product. Accordingly, the invention includes this additional modified alumina treatment specifically targeted for $H_2S$ and COS removal. The modified alumina used in this second treatment should possess an affinity for $H_2S$ and COS, a non-limiting example of which is sold under the trademark SELEXSORB-COS by ALCOA. The manner in which the propylene feed and second modified alumina are contacted is not particularly limited, so long as the contacting is sufficient to remove at least a portion of the $H_2S$ and COS present. It is preferred that the first modified alumina treatment precede the second so that contaminants that might interfere with the adsorptive specificity of the second modified alumina are removed during the first modified alumina treatment.

The contacting of the propylene feedstock with alumina, a molecular sieve, and the two modified aluminas may be accomplished by any means that enables purification of the feed. A preferred method is the use of granular absorptive materials in adjacent packed beds, though fluidized beds or other contacting means may be employed.

The pre-treated benzene feed and pre-treated propylene feed are reacted in the presence of a zeolite catalyst to form cumene. The reaction may be carried out in any reactor and under reaction conditions that are conducive to cumene synthesis. Preferably, the reaction is carried out in a flow reactor comprising a fixed bed of zeolite catalyst under liquid phase conditions at a hourly space velocity of about 5/hr to 70/hr, at a temperature in the range of about 250 to 350° F., preferably about 275 to 300° F., and at a pressure of about 200 to 500 psig to maintain the reactants and product in a liquid phase. The zeolite catalyst utilized is not particularly limited so long as it can effectively catalyze the reaction. Examples of suitable zeolite catalysts include beta zeolites, Y-zeolites, ZSM-zeolite and MCM-22 zeolite. An MCM-22 zeolite is preferred.

With reference to the FIGURE, the invention will now be described in terms of a preferred embodiment. The preferred embodiment is not intended to limit the scope of the invention defined in the appended claims.

The FIGURE is a schematic of a cumene synthesis unit capable of performing a cumene synthesis process in accordance with the invention. Benzene feedstock containing olefinic contaminants is introduced into hot clay treater 11 containing a bed of hot clay to convert the olefinic contaminants into higher boiling polymers, alkylaromatics or other hydrocarbons. The benzene feed is then introduced into distillation column 12, where the higher boiling converted olefinic contaminants are separated and removed from the benzene feed. The benzene feed is then sequentially introduced into cold clay treaters 13 and 14, where nitrogen-containing poisons are removed from the benzene feed through contact with ambient-temperature clays.

The propylene feedstock is introduced into a vertical treater housing multiple treatment stages 21, 22, 23 and 24. The propylene feedstock is introduced into the bottom of the treater and is caused to flow upwardly to minimize the amount of moisture-and-contaminant-rich mist associated with the feedstock from entering the treater. The propylene feedstock first enters treatment stage 21, and there contacts a bed of alumina capable of removing trace sodium compounds and moisture from the feed. The feed then flows into adjacent treatment stage 22 which comprises bed of a zeolite molecular sieve. The feed contacts the molecular sieve, which removes additional moisture from the feed. Immediately downstream from treatment stage 22 is a bed of modified alumina comprising treatment stage 23. The propylene feed contacts the bed of modified alumina, which removes nitrogen-, sulfur- and oxygen-based poisons from the feed. Finally, the feed contacts a bed of second modified alumina in treatment stage 24, which selectively removes hydrogen sulfide and carbonyl sulfide from the propylene feed.

The pre-treated benzene and propylene feeds are introduced into reactor 30, which houses a zeolite catalyst. The benzene and propylene react, catalyzed by the zeolite, to form cumene. The pre-treatment of the feedstocks removes at least a portion of the zeolite catalyst poisons contained in the untreated feeds, thereby extending the life and enhancing the catalytic activity of the zeolite catalyst.

Though the invention has been described above with reference to specific embodiments, other embodiments of the invention can readily be envisioned by one of ordinary skill in the art in light of this teaching. Modifications, substitutions, changes and/or omissions may be made without departing from the spirit and scope of the invention defined in the appended claims.

We claim:

1. A method of improving the activity and lifetime of a zeolite catalyst in a process for synthesizing cumene, said method comprising:

a) pre-treating a benzene feedstock containing catalyst poisons comprising olefinic compounds, said benzene feedstock pre-treating comprising:

contacting said benzene feedstock with a clay to convert said olefinic compounds contained in said benzene feedstock to polymers, alkylaromatics and other hydrocarbons having a higher boiling point than benzene, said clay being at a temperature within the range of about 200 to 500° F., said benzene feedstock being under a pressure during said contacting with said clay to maintain said benzene feedstock in a liquid phase;

distilling said benzene feedstock after said contacting with said clay, to separate said benzene feedstock from said polymers, alkylaromatics and other hydrocarbons having a higher boiling point than benzene;

b) pre-treating a propylene feedstock, said propylene feedstock containing trace sodium compounds, trace moisture and catalyst poisons comprising nitrogen-containing compounds, sulfur-containing compounds and oxygen-containing compounds, said propylene feedstock pre-treating comprising:

contacting said propylene feedstock with an alumina to remove said trace sodium compounds and a first portion of said trace moisture;

contacting said propylene feedstock with a molecular sieve to remove a second portion of said trace moisture;

contacting said propylene feedstock with a first modified alumina to remove said nitrogen-containing compounds, said oxygen-containing compounds and a first portion of said sulfur-containing compounds, said contacting with said first modified alumina occurring after said contacting with said alumina and said contacting with said molecular sieve;

contacting said propylene feedstock with a second modified alumina to remove a second portion of said sulfur-containing compounds, said second portion of said sulfur-containing compounds comprising hydrogen sulfide and carbonyl sulfide;

c) reacting said pre-treated benzene with said pre-treated propylene in the presence of a zeolite catalyst to form cumene.

2. The process according to claim 1, wherein said clay is at a temperature within the range of about 350 to 500° F.

3. The process according to claim 1, wherein said clay is at a temperature within the range of 350 to 375° F., and said benzene feedstock is under a pressure of about 200 psig during said contacting with said clay.

4. The process according to claim 1, wherein said zeolite catalyst is an MCM-22 zeolite.

* * * * *